US00PP12124P2

(12) United States Plant Patent
Bak et al.

(10) Patent No.: US PP12,124 P2
(45) Date of Patent: Oct. 9, 2001

(54) GUZMANIA PLANT NAMED 'TEMPO'

(75) Inventors: Elly Bak, Rijsenhout; Nicolaas D. M. Steur, Oude Niedorp, both of (NL)

(73) Assignee: Corn Bak. B.V., Assendelft (NL)

( * ) Notice: Subject to any disclaimer, the term of this patent is extended or adjusted under 35 U.S.C. 154(b) by 0 days.

(21) Appl. No.: 09/343,211

(22) Filed: Jun. 30, 1999

(51) Int. Cl.[7] ..... A01H 5/00
(52) U.S. Cl. ..... Plt./371
(58) Field of Search ..... Plt./371

(56) References Cited

PUBLICATIONS

UPOV–ROM GTITM Computer Database 2000/2, GTI Jouve Retrieval Software, Citations for Guzmania named 'Tempo', 2000.

*Primary Examiner*—Bruce R. Campell
*Assistant Examiner*—Melissa L. Kimball
(74) *Attorney, Agent, or Firm*—Foley & Lardner

(57) ABSTRACT

A Guzmania plant named 'Tempo' particularly characterized by its solid, compact growth habit in a funnel-form rosette; numerous, relatively narrow leaves; superior floral bract production; star-shaped inflorescence; bright, relatively deep red floral bracts; and long-lasting habit.

1 Drawing Sheet

BACKGROUND OF THE INVENTION

The present invention comprises a new and distinct cultivar of Guzmania that is a hybrid, hereinafter referred to by the cultivar name 'Tempo'.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short lived.

Guzmania may be advantageously grown as pot plants for greenhouse or home use. Desirably, the plants are shaded from direct sunlight; and, during the spring to autumn period, the central vase-like part of the leaf rosette is desirably filled with water.

Guzmania is native to tropical America. Leaves of Guzmania are usually formed as basal rosettes which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots produced by the plant which may then be rooted. The resulting plantlets are detached from the mother plant and may be potted in a suitable growing mixture.

Methods for cultivation and crossing of Guzmania are well known. For a detailed discussion, reference is made to the following publications, which are incorporated herein by reference: Benzing, David H., *The Biology of the Bromeliads*, Mad River Press, Inc., Eureka (1980); Zimmer, Karl, *Bromelien*, Verlag Paul Parey, Berlin (1986); and Rauh, Werner, *Bromelien*, Verlag Eugen Ulmer, Stuttgart (1981).

The new cultivar 'Tempo' is a product of a planned breeding program and was originated by the inventors from a cross made during such a program in Assendelft, The Netherlands, in 1993. The male or pollen parent was a proprietary selection of *Guzmania lingulata minor* identified by Code No. 93523011 . The female or seed parent was a proprietary selection of *Guzmania lingulata lingulata* identified by Code No. 93523272.

The selection which is the variety 'Tempo' was chosen after commencement of flowering of the progeny of the cross of 93523011×93523272 in 1996 in Assendelft, The Netherlands. The selection was first asexually propagated through offshoots by, or under the supervision of, the inventors in Assendelft, with subsequent asexual reproduction through offshoots. Continuous asexual propagation has demonstrated that the combination of characteristics as herein disclosed for the new cultivar 'Tempo', as observed in Assendelft, The Netherlands, are firmly fixed and are retained through successive generations of asexual reproduction.

Both parents have a degree of homozygosity such that the progeny of the cross 93523011×93523272 are phenotypically uniform and identical to 'Tempo'. Accordingly, plants which are phenotypically identical to 'Tempo' can be produced by sexual reproduction as well as asexual reproduction.

'Tempo' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar. For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The closest comparison cultivar is Guzmania 'Intro'. The most important difference is the color of the inflorescence. Guzmania 'Tempo' is red (RHS 44A) and Guzmania 'Intro' is gray-purple (RHS 185A).

BRIEF SUMMARY OF THE INVENTION

'Tempo' is particularly characterized by the following characteristics:

1. Solid, compact growth habit in a funnel-form rosette measuring approximately 19 cm in height above the pot when flowering; the cultivar is small both in height and overall diameter;
2. Numerous, relatively narrow leaves, each approximately 2–3 cm in width and 21 cm in length;
3. Superior floral bract production;
4. Star-shaped inflorescence;
5. Floral bracts are a bright, relatively deep red, which especially distinguishes the new cultivar from others, including the cultivar 'Intro' disclosed in U.S. Plant Pat. No. 10,852; and
6. Long-lasting habit.

BRIEF DESCRIPTION OF THE DRAWING

In the accompanying color photographic drawing, sheet 1 is a side view of a specimen of 'Tempo' showing the primary and top bracts.

DETAILED BOTANICAL DESCRIPTION

The following traits have been repeatedly observed and in combination distinguish 'Tempo' as a new and distinct cultivar. 'Tempo' was asexually propagated from offshoots and was approximately 10 months old at the time of observation. These observations, measurements and descriptions were taken for 'Tempo' plants grown under the following greenhouse conditions in Assendelft, The Netherlands:

The minimum day and night temperatures were 20 and 18° C., respectively. The ventilation temperature was 24° C., and the maximum light intensity was 18000 Lux. Fertilizer concentration was 0.5 to 1 EC comprising N:P:K in the ratio of 1:0.25 to 0.5:2 to 3. In addition, 3% of the total amount of fertilizer was $MgSO_4$.

Frequency of fertilization varied depending on time of year and ranged from once per week to once per month. Fertilization was more frequent during the spring and summer months. Following fertilization, the plants were rinsed with sufficient clean water to remove residual fertilizer from the leaves.

With regard to induction of flowering, acetylene gas is allowed to bubble through 100 L of cool water for 30 min. at a pressure of 0.5 bar. Whole plants are then sprayed with the acetylene solution, making certain that the cup (vase) is filled. Spraying is done in the morning because the plants need light after this treatment, and the plants are not watered again for at least two days. The plants are treated again, following this same protocol, one week later. Plants should not be fertilized for two to three weeks following treatment with acetylene because it is likely the flowers will not form and the bracts will remain green.

In the following description, color references are made to The Royal Horticultural Society (R.H.S.) Colour Chart:

Plant:

*Form.*—Funnel-form rosette.

*Height.*—Approximately 19 cm high, when flowering.

*Growth habit.*—Stemless.

*Diameter.*—Approximately 40 cm.

*Variation.*—The foregoing dimensions can vary substantially depending on the timing of the acetylene treatment to induce flowering. When the plant is treated as a relatively small plant, the height and diameter of the plant will be smaller than if acetylene treatment is carried out on a much older and larger plant. This is well-known to those skilled in the art, with size of plant being controlled by the grower based on the timing of the acetylene treatment.

Foliage:

*Color (upper surface).*—Between RHS 144A–146A.

*Color (under surface).*—Between RHS 146B–146C (the color of leaves can change depending on environmental conditions).

*Size of leaf.*—Length is approximately 21 cm and width is approximately 2–3 cm.

*Shape of leaf.*—Linear-lanceolate.

*Surface texture.*—Smooth.

*Orientation.*—Leaf blades arch continuously from base.

*Variegation.*—None.

Bracts:

*Length.*—Scape bracts: The lowest approximately scape bracts are approximately 14 cm long. The scape bracts just below the primary bracts are approximately 9 cm long. Primary bracts: The lowest primary bracts are approximately 10 cm long. The bracts progress upwardly, they become shorter, with the top primary bracts being approximately 5 cm in length.

*Width.*—The scape bracts are approximately 3–3.5 cm wide and the primary bracts are approximately 3 cm wide.

*Number.*—There are approximately 8 scape bracts and 14 primary bracts, which combine to make a full inflorescence.

*General shape.*—Recurved and ovate-lanceolate.

*Texture.*—Smooth.

*Margin.*—Entire.

*Color.*—The primary bracts are RHS 44A and the tip of the top primary bracts is RHS 17A. The color of the scape bracts is RHS 44A.

Inflorescence:

*Borne (stalks).*—Erect.

*Shape of inflorescence.*—Singular (head).

*Size of inflorescence on stalk.*—The size of the inflorescence changes with maturity; at full flowering, inflorescence is approximately 7 cm in height and approximately 13 cm in diameter.

Flowers:

*Individual petals.*—(Mostly disposed within the inflorescence). Length: Approximately 5.5 cm. Width: Approximately 0.5 cm. Quantity: Approximately 25 flowers depending on the size of the plant. Colour: RHS 17A with a white top. Time of Blooming: A fully grown plant can bloom the whole year starting approximately 15 weeks after natural induction or through treatment with acetylene. Duration of blooms: Each flower blooms one (1) day and the total length of blooming of the whole inflorescence is 4 weeks.

Reproductive organs:

*Ovaries.*—Superior.

*Stamens.*—Six (6) in number.

Seed characteristics:

*Quantity.*—Approximately 5000 seeds divided over approximately 20 capsules (depending on the size of the plant).

*Texture.*—The seeds are plumose.
*Seed color.*—RHS 165B.
*Pappus color.*—RHS 165 D.
*Other.*—This cultivar is a hybrid and, therefore, the seeds cannot be used for reproduction of 'Tempo'.

I claim:

1. A new and distinct cultivar of Guzmania plant named 'Tempo', substantially as illustrated and described.

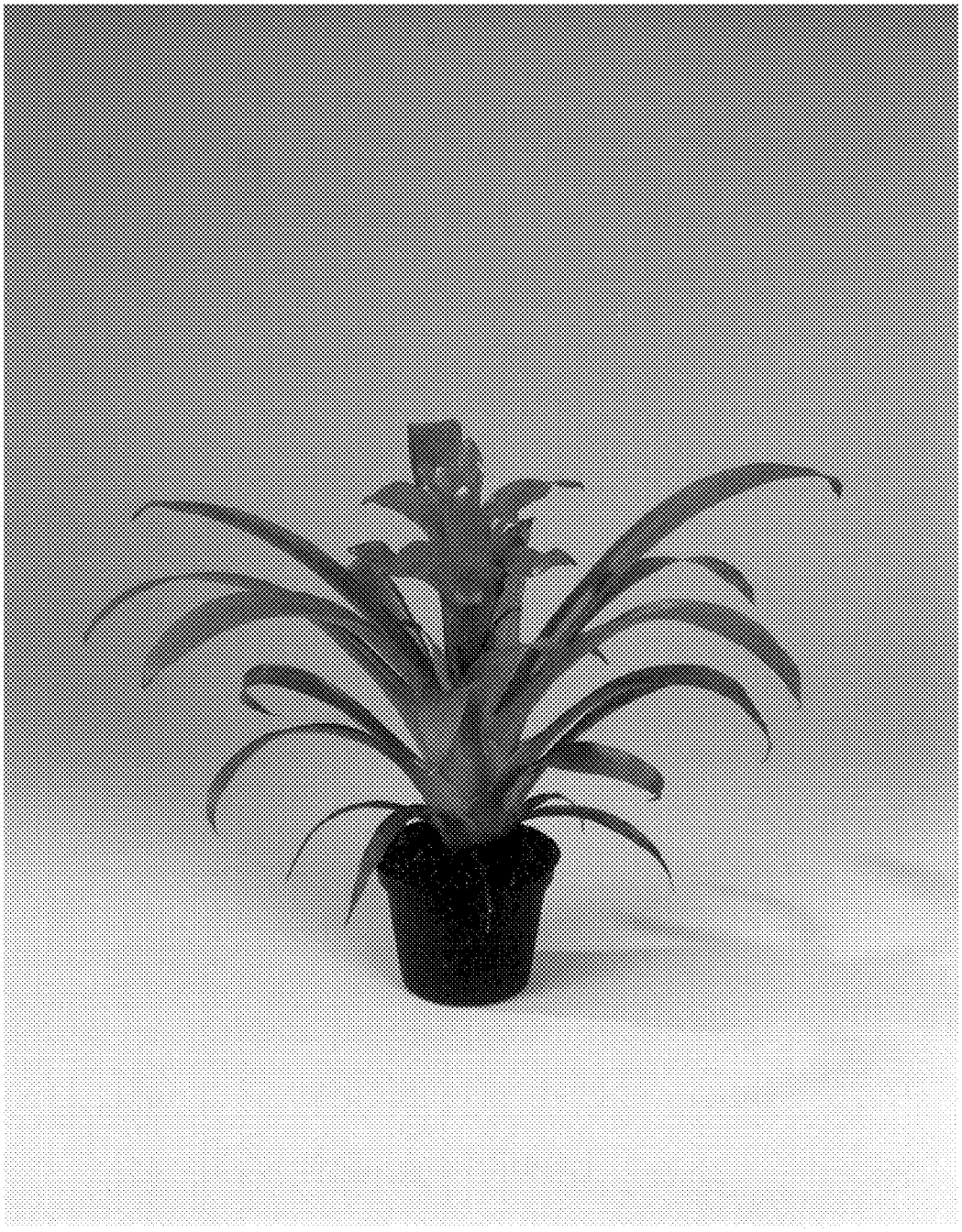

* * * * *